United States Patent [19]

Takeo et al.

[11] Patent Number: 4,764,507

[45] Date of Patent: Aug. 16, 1988

[54] POLYSACCHARIDE RDP SUBSTANCE

[75] Inventors: Suguru Takeo, Yokohama; Hisao Kado, Tokyo; Nobuhiro Watanabe, Kishi; Kiichi Uchida, Fujisawa; Yoshitada Mori, Tokyo, all of Japan

[73] Assignees: Sapparo Breweries Limited, Tokyo; Daicel Chemical Industries, Ltd., Sakai; Etsuo Ito, Urasoe, all of Japan

[21] Appl. No.: 586,073

[22] Filed: Mar. 5, 1984

[30] Foreign Application Priority Data

Mar. 18, 1983 [JP] Japan .................. 58-44316

[51] Int. Cl.⁴ .................. A61K 31/73; C08B 37/00
[52] U.S. Cl. .................. 514/54; 514/23; 536/1.1; 536/55.1; 536/128; 435/72
[58] Field of Search .................. 514/23, 25, 59; 536/1.1, 55.1

[56] References Cited

U.S. PATENT DOCUMENTS

| 2,900,284 | 8/1959 | Oshima et al. | 536/1.1 |
| 4,182,756 | 1/1980 | Ramsay et al. | 536/1.1 |
| 4,357,323 | 11/1982 | Soma et al. | 536/1.1 |
| 4,366,308 | 12/1982 | Soma et al. | 536/1.1 |

*Primary Examiner*—Ronald W. Griffin
*Assistant Examiner*—Elli Peselev
*Attorney, Agent, or Firm*—Frishauf, Holtz, Goodman & Woodward

[57] ABSTRACT

A polysaccharide RDP substance having the ultraviolet absorption spectrum depicted in FIG. 1, the infrared absorption spectrum depicted in FIG. 2 and the $^{13}$C-NMR spectrum depicted in FIG. 3 is obtained from rice bran by extraction.

2 Claims, 3 Drawing Sheets

POLYSACCHARIDE RDP SUBSTANCE

BACKGROUND OF THE INVENTION

1. Field of the Invention

This invention relates to a novel polysaccharide RDP substance and antitumor agent, immunomodulating agent, and host defense agent against infectious disease containing said substance as the effective component.

2. Description of the Prior Art

As is known in the art, polysaccharides are obtained from various sources, for example, Basidiomycetes (Japanese Patent Kokai Koho No. 94012/1978), bacteria (Japanese Patent Kokai Koho No. 76896/1979), mould (Japanese Patent Publication No. 59097/1978), algae (Japanese Patent Kokai Koho No. 28923/1977), and grains (Japanese Patent Kokai Koho No. 139713/1978).

It is also known that these polysaccharides have antitumor activity. However, various problems, for example, low yields, complicated production process, toxicity, etc., are encountered in using such polysaccharides as an antitumor agent.

SUMMARY OF THE INVENTION

According to the present invention, it has been found that a novel polysaccharide RDP substance can be obtained from rice bran, and that the polysaccharide RDP substance is effective as an antitumor agent, an immunomodulating agent against transplantable tumors, and host defense agent against infectious disease.

The present invention relates to:

(1) a novel polysaccharide RDP substance;

(2) a process for producing the polysaccharide RDP substance of (1) which comprises the steps of:

treating a rice bran with hot water to extract said polysaccharide RDP substance into the water, adding a polar organic solvent or a salting-out agent to the water containing the extracted substance to form precipitates containing said polysaccharide RDP substance, isolating the precipitates, and subjecting the precipitates to a deproteinizing treatment;

(3) a pharmaceutical composition effective in inhibiting the growth of tumors of mice containing the polysaccharide RDP substance of (1) as an effective ingredient;

(4) a pharmaceutical composition effective in modulating the immunological state of mice containing the polysaccharide RDP substance as an effective ingredient; and (5) a pharmaceutical composition effective in potentiating the host defense ability against infectious microorganisms containing the polysaccharide RDP substance as an effective ingredient.

DETAILED DESCRIPTION OF THE INVENTION

Figure 1:
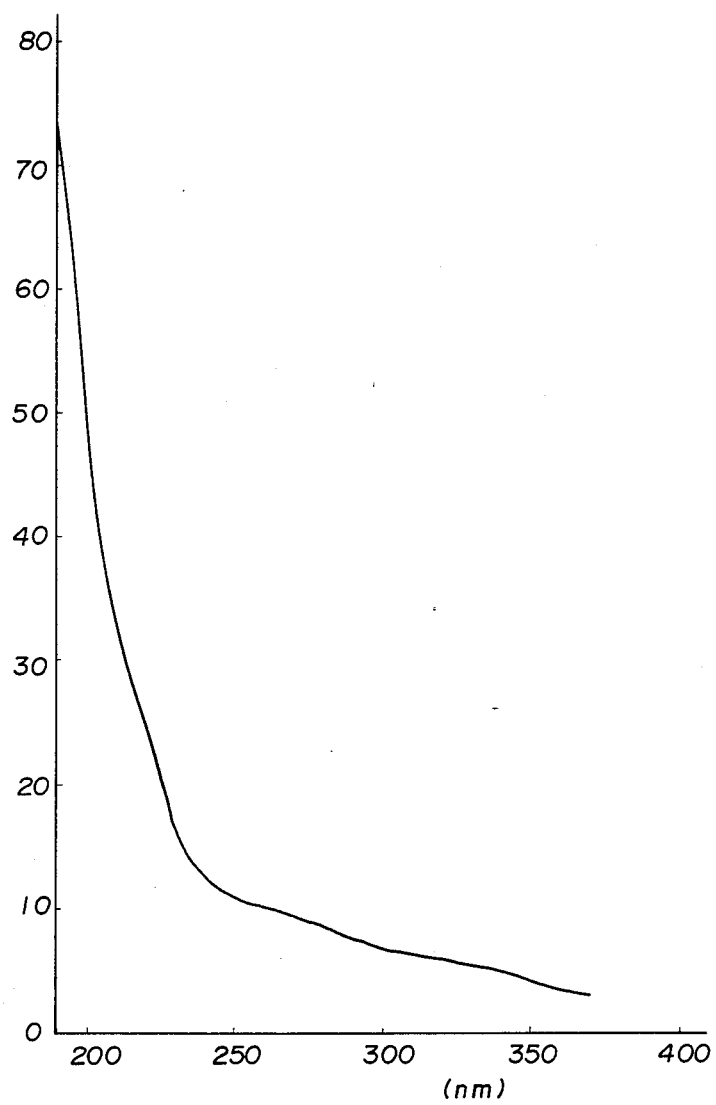
FIG. 1 is an ultraviolet absorption spectrum of the polysaccharide RDP substance produced by the process of the present invention.

This invention relates to a novel polysaccharide RDP substance, a process for the production of said substance, and antitumor agent, immunomodulating agent against transplantable tumors, and host defense agent against infectious disease containing said substance as the effective component.

The polysaccharide RDP substance of this invention is obtained from rice bran by extraction and purification. This rice bran is a by-product obtained in the production of polished rice from unpolished rice, and it is not limited by the variety of the unpolished rice, the producing district, the degree of polishing rate, etc. Prior to the extraction and purification of the polysaccharide RDP substance from the rice bran, it is desirable to fully wash the rice bran in order to eliminate the pulverized (or crushed) rice and other impurities. Those rice brans which have already been used for other purposes, such for example as defatted rice bran, which is a residue after extraction of rice-bran oil from rice bran, can be used in this invention.

The polysaccharide RDP substance of this invention is produced by adding organic solvents or salting-out agents to an extract obtained by hot water-treatment of rice bran to provide precipitates and, if desired, dissolving the obtained precipitates in water to purify them.

The rice bran is passed through a separator, for example, a screen, to remove impurities and is washed with water, if necessary, after pulverization. It is desirable to remove a lipid soluble fraction using organic solvents, such as ethyl acetate, carbon tetrachloride, chloroform, ether, n-hexane, benzene, petroleum ether, acetone etc.

The hot water-treatment of the rice bran is carried out by feeding rice bran and distilled or purified water in amount of about 5–10 times to that of the rice bran to a vessel or a pressure vessel, such for example as a stainless steel tank, an enameled tank, a glass tank, a flow system tubular extraction device and the like with or without stirring under the conditions of pressure of from 0 to 15 kg/cm$^2$, preferably from 0 to 5.0 kg/cm$^2$ and a temperature of from 70° C. to 200° C., preferably from 100° C. to 150° C. for 10 minutes to 24 hours, preferably 0.5 to 5 hours. Practically it is suitable to carry out the hot water-treatment at a pressure of from 0 to 3.0 kg/cm$^2$ and a temperature of from 100° C. to 140° C. for 1 to 5 hours.

The extract obtained by the hot water-treatment is subjected to operations such as filtration, centrifugation, etc. to separate solids and, if necessary, is then concentrated to an appropriate volume by applying such means as concentration at a reduced pressure, ultrafiltration, etc., singly or in combination with each other.

By collecting precipitates formed by adding a water-soluble polar organic solvent or a salting-out agent to the extract, a crude polysaccharide RDP substance is obtained.

Polar organic solvents which can be used in this procedure include methanol, ethanol, propanol, acetone, etc. The amount of the polar organic solvent being used is determined taking into account the amount of the desired substance contained in the extract, etc. For example, in the case of ethanol, it may be added in such a manner that the ethanol concentration is 30 to 50% (v/v). The formed precipitates are preferably washed with the organic solvent as described above, for example, ethanol, etc.

Salting-out agents which can be used in the above procedure include sodium chloride, ammonium sulfate, and potassium chloride. The salting-out agent is usually added until the degree of saturation reaches 0.5 to 1 to thereby form precipitates.

The deproteinization and purification of the polysaccharide RDP substance can be carried out either prior to the addition of the organic solvent or salting-out agent to the extract or after the formation of precipitates by the addition of the organic solvent or salting-out agent followed by dissolving the precipitates in water.

For the purification and deproteinization treatment, various known-procedures can be applied. For example, amylolytic enzyme and/or proteolytic enzyme is added to a solution containing the polysaccharide RDP substance to convert impurities existing therein, such as starch, protein, etc., into low molecular weight compounds. These low molecular weight compounds are removed at a subsequent purification step.

As such enzymes, an amylolytic enzyme, for example α-amylase, iso-amylase, pullulanase, etc., a proteolytic enzyme, for example papain, pepsin, trypsin, pronase, etc., and if necessary, other enzymes can be used. In this enzyme treatment, it is preferred that the enzyme is added in a ratio of from 1/1000 to 1/5000 of the substrate and that the treatment is carried out for 0.5 to 24 hours, preferably 1 to 15 hours.

Additionally, the following purification and deproteinization methods can be used: a method in which an inorganic or organic acid, such as glacial acetic acid, sulfuric acid, hydrochloric acid, tannic acid, trichloroacetic acid, etc. is added to an aqueous solution containing the above described polysaccharide RDP substance in a proportion of about 0.1 to 10 wt. %, preferably about 3 to 5 wt. %. When precipitates are formed, they are removed by such operations as filtration, centrifugation, etc. and subsequently the remaining acids, inorganic ions and low molecular fractions are dialyzed for 1 to 3 days against running water or distilled water using a semipermeable membrane, such as cellophane membrane, collodion membrane or the like; an ion exchange method in which a cation or anion exchanger, such as Dowex, Amberlite, Duolite, Diaion or the like, is used; an ultrafiltration method in which a membrane having a fractional molecular weight of 1,000 to 100,000 is used; gel filtration; centrifugation; treatment with active carbon; concentration and a combination thereof. Furthermore the RDP substance can be hydrolyzed using acids and/or some enzymes to molecular weights of 1,000,000 to 10,000 maintaining the biological activities. A large amount of protein can be removed from polysaccharide RDP substance by the above-described methods. However, a small amount of protein that bounds chemically to the polysaccharide RDP substance cannot be removed completely. In this case, it is possible to remove protein completely from polysaccharide RDP substance by such a method as Sevag's.

These purification methods can be applied singly or in combination with each other, and such combinations and the order in which they are applied are subject to no limitations.

By lyophilizing or spray-drying an aqueous solution containing the high molecular polysaccharide RDP substance which has been purified by the above described methods, a white RDP substance in a powdery form can be obtained.

The thus obtained polysaccharide RDP substance has the following physical and chemical properties:

This substance does not pass through a dialysis membrane and is insoluble in organic acids or organic solvents, for example, glacial acetic acid, alcohols such as methanol, ethanol, propanol, butanol, etc., acetone, hexane, benzene, ethylacetate, dimethylsulfoxide, ligroin, carbon tetrachloride, chloroform, and ethers, but is soluble in water;

A 1% aqueous solution of the present substance is neutral.

The present substance has no melting point and it turns brown at 220° C. and black at 280° C. (carbonizing); Elemental analysis shows that the present substance obtained in Example 1 as described later comprises 38.10% of carbon, 6.27% of hydrogen, 50.73% of oxygen and 4.90% of ash.

A 1% aqueous solution of the present substance is positive in the following color reactions: phenol-sulfuric acid reaction, anthrone-sulfuric acid reaction, carbazole-sulfuric acid reaction, tryptophane-sulfuric acid reaction, cystein-sulfuric acid reaction, chromotrope-sulfuric acid reaction and the Molisch reaction, and negative in the following color reaction: biuret reaction, ninhydrin reaction, the Lowry-Folin reaction,the Elson-Morgan reaction,and starch-iodine reaction;

The specific rotation of the present substance obtained in Example 1 as described later is $[\alpha]_D^{20} = +142°$ to $+145°$ (H$_2$O);

It has been confirmed that the ash component comprises Si, P, K, Na, Ca, Mg, etc. and on the ground of the fact that the RDP substance is eluted in void volume on gel filtration using Sepharose CL-6B (produced by Pharmacia Chemicals AB), it is assumed that the above elements do not exist independently as an element or compound thereof in the RDP substance, but that they exist in the state that they are bound to a skeleton of the RDP substance;

The supernatant liquid obtained by a method which comprises hydrolyzing RDP substance with 1 N sulfuric acid, at 100° C. for 3 hours and then adding barium carbonate to neutralize, is positive in the following color reactions: the Molisch reaction, anthrone reaction, tryptophane-sulfuric acid reaction, cystein-sulfuric acid reaction, chromotrope-sulfuric acid reaction and the like, and negative in the following color reactions: biuret reaction, ninhydrin reaction, the Lowry-Folin reaction and the like;

In the above hydrolysate, glucose was always detected by thin layer chromatographic analysis. On developing with the four solvents as noted below in the thin layer chromatographic analysis of those products obtained by complete hydrolysis of the RDP substance with formic acid and sulfuric acid, no spots except for the one identified as glucose could be detected.

(1) ethyl acetate :methanol:acetic acid:water (65:15:10:10)

(2) ethyl acetate:isopropanol:water (65:23:12)

(3) isopropanol:pyridine:water:acetic acid (8:8:4:1)

(4) n-butanol:pyridine:water (6:4:3) Thus it can be concluded that the present RDP substance is a polysaccharide consisting essentially of glucose as a sole sugar component.

Figure 2:
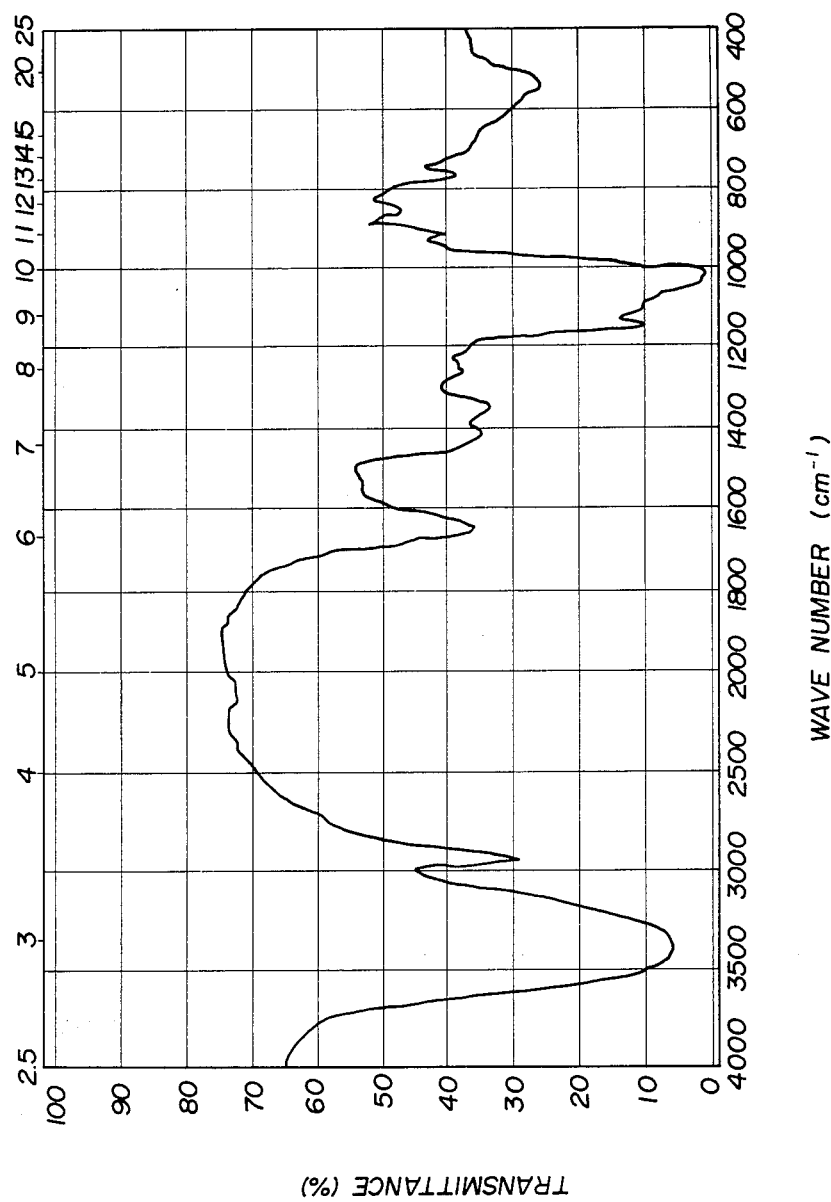
FIG. 2 is an infrared absorption spectrum of said polyschardie RDP substance.
Figure 3:
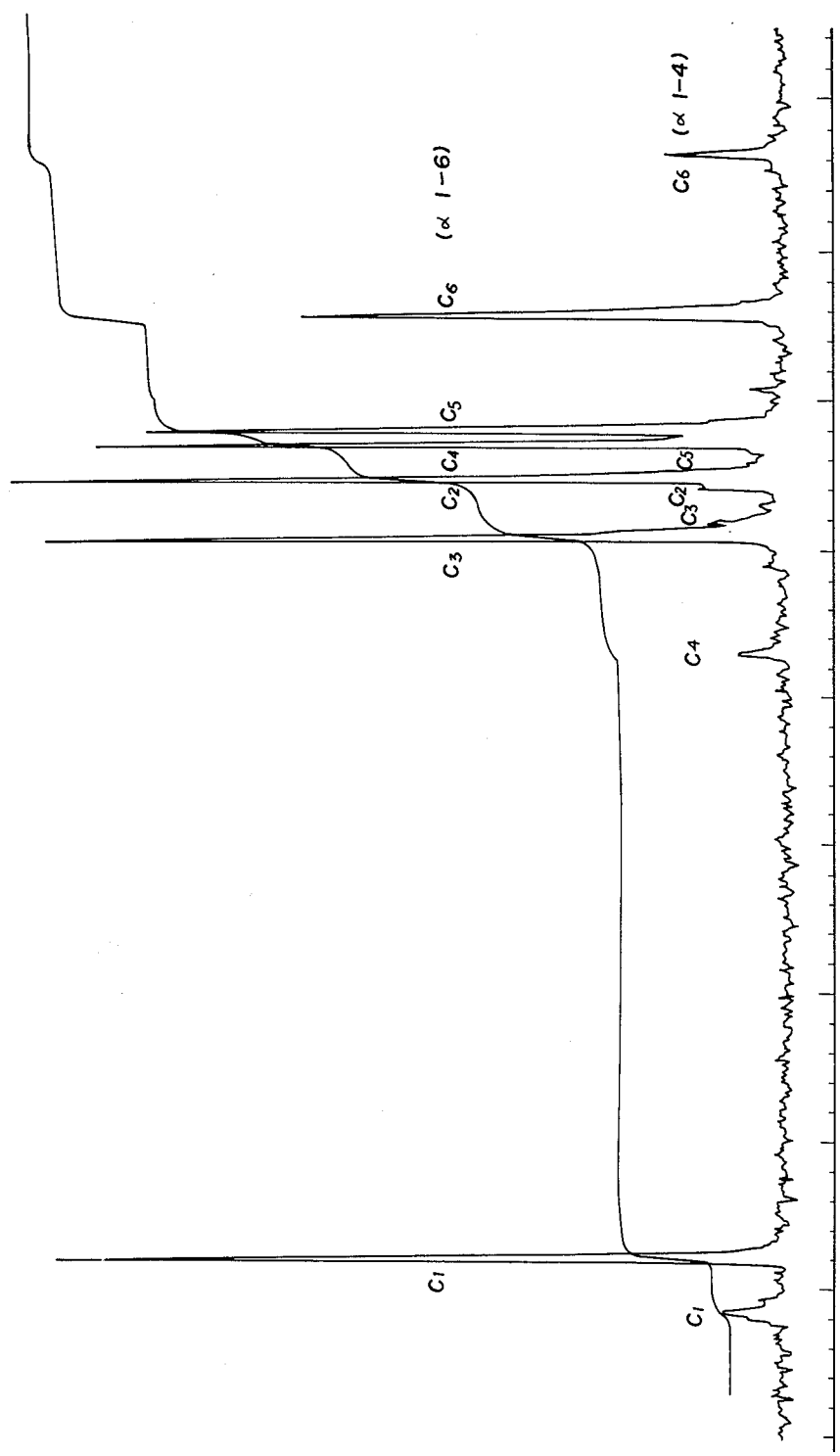
FIG. 3 is a $^{13}C$-NMR spectrum of said polysaccharide RDP substance.

The present RDP substance has an ultraviolet absorption spectrum as shown in FIG. 1, an infrared absorption spectrum as shown in FIG. 2, and a $^{13}$C-NMR spectrum as shown in FIG. 3. From the infrared absorption spectrum and specific rotation, it is assumed that the α-bound exists in the RDP substance.

Based upon the above described data, it is assumed that the RDP substance of this invention is a polysaccharide comprising glucose as a sole sugar component.

Moreover, on periodate oxidation, the present RDP substance consumed 1.7 mole of sodium periodate and released 0.85 mole of formic acid per glucose residue. The Smith-degradation procedure of this substance gave glycerine detected by paper chromatographic analysis. Methylation analysis of this substance yielded 2,3,4-tri-O-methyl-D-glucose together with a small amount of tetramethyl and dimethyl glucose derivatives.

Based upon the above described data, it is assumed that the RDP substance of this invention is a polysaccharide which has α-1,6-glucoside bond as the main chain. Furthermore, the $^{13}$C-NMR analysis of the present RDP substance showed the presence of α-1,6-linked glucose residues and much smaller amount of α-1,4-linked glucose residues.

It has been made clear that the polysaccharide RDP substance of this invention has various biological activities such as antitumor against transplantable tumors, immunomodulating, and host defense activities against infectious microorganisms. The methods and results of testing these biological activities of the polysaccharide RDP substance produced in the Example 1 will be described in detail.

(1) Antitumor Activities (a) Effect of Intraperitoneal Administration of RDP Substance Against a Syngeneic Tumor Meth-A Fifty 6-week-old female BALB/C-CRJ mice (average weight, 20 grams (g)) were transplanted with tumor cells ($1 \times 10^5$ cells/mouse) intraperitoneally, which had been grown for one week intraperitoneally in the mouse of the same strain. These mice were divided into four groups; a group of 20 mice as a control group and three groups of 10 mice each as test groups. For 5 consecutive days from the day after the transplantation of the tumor cells, the RDP substance dissolved in a saline was administered intraperitoneally in a dose of 10, 30 or 100 milligrams per kilogram (mg/kg) for the test groups. For the control group, on the other hand, only a saline was administered in the same manner. The survival time (days) was measured and the prolongation of life was calculated by the following equation:

$$\text{Prolongation of life (\%)} = \frac{\text{Average survival time (days) for test group}}{\text{Average survival time (days) for control group}} \times 100$$

(b) Effect of Oral Administration of RDP Substance Against a Syngeneic Tumor Meth-A Fifty 6-week-old female BALB/C-CRJ mice average weight, 20g) were transplanted with tumor cells ($1 \times 10^4$ cells/mouse) subcutaneously in the axillary region, which had been grown for one week intraperitoneally in the mouse of the same strain. These mice were divided into four groups; a group of 20 mice as a control group and three groups of 10 mice each as test groups. For 10 consecutive days from the day after the transplantation of the tumor cells, the RDP substance dissolved in a saline was administered orally in a dose of 10, 30 or 100 mg/kg, for the test groups. For the control group, on the other hand, only a saline was administered in the same manner. Thirty-five days after the transplantation of the tumor cells, the mice were killed and the tumor developed was cut away and weighed. The inhibition ratio was calculated by the following equation:

$$\text{Inhibition ratio (\%)} = \left(1 - \frac{\text{Average weight of tumor for test group}}{\text{Average weight of tumor for control group}}\right) \times 100$$

The antitumor activities of the RDP substance as assayed by the above-described methods (a) and (b) are shown in the Table I.

TABLE I

| Sample | Dose (mg/kg) | Intraperitoneal Administration (a) | | Oral Administration (b) | |
|---|---|---|---|---|---|
| | | Average Survival Time (days) | Prolongation of Life (%) | Average Tumor Weight (g) | Inhibition Ratio (%) |
| Control (Saline) | — | 21.0 | — | 9.30 | — |
| RDP Substance | 10 | 27.3 | 130 | 5.12 | 45 |
| | 30 | >42.0 | >200 | 3.72 | 60 |
| | 100 | 35.7 | 170 | 4.65 | 50 |

From the results shown in the Table I, it can be seen that the RDP substance exhibits a strong antitumor activity against a tumor of mice with the optimum dose of about 30 mg/kg both by intraperitoneal and by oral administration.

In addition, it has been confirmed using mice that the RDP substance was also effective against Lewis lung carcinoma, Melanoma B-16, Sarcome 180, and Ehrlich ascites carcinoma, within a dose range of from 10 to 100 mg/kg by intraperitoneal or oral administration with the results that the tumor inhibition ratio was from 30 to 70%. Furthermore, the RDP substance is of no toxicity as described hereinafter. Thus the RDP substance is believed to find use as a very effective antitumor agent.

(2) Immunomodulating Activities (a) Carbon Clearance Test (CCT)

This test is used to examine the effect of the RDP substance to enhance the phagocytic activity of macrophage amongst the immunomodulating actions.

The RDP substance dissolved in a saline was administered intraperitoneally to a test group of six 4-week-old female ICR-CRJ mice (average weight, 20 g) for 2 days. On the other hand, only a saline was administered for the control group in the same manner. At the third day, 0.25 ml of a carbon solution (prepared by diluting a black ink—Fount India manufactured by Perikan Co.— with a saline to 5 times) was injected into the tail vein. Just after the injection and also 10 minutes after the injection, 0.025 ml of blood was collected from the venous plexus of the retro-orbit of the mice, suspended in 3.5 ml of a 0.01 M sodium carbonate solution, and the absorbance ($OD_{650}$) at 650 nm was measured to determine a rate of decrease in the concentration of the carbon in the blood. This is indicated by a phagocytic index as defined by the following equation:

mined by the method of Cunningham. The results are shown in the Table III.

TABLE III

| Sample | Dose (mg/kg) | Sensitization on 4th day | | Sensitization on 11th day | |
|---|---|---|---|---|---|
| | | Number of Plaques per Spleen | Relative Value (%) | Number of Plaques per Spleen | Relative Value (%) |
| Control (Saline) | — | $2.7 \times 10^4$ | 100 | $2.4 \times 10^4$ | 100 |
| RDP Substance | 10 | 4.1 | 150 | 6.0 | 250 |
| | 30 | 7.0 | 260 | 8.6 | 360 |
| | 100 | 6.3 | 233 | 8.1 | 337 |

$$\text{Phagocytic index} = \frac{\log C_1 - \log C_2}{T_2 - T_1}$$

where $C_1$ is an absorbance ($OD_{650}$) at the time $T_1$ and $C_2$ is that at the time $T_2$.

With regard to tumor-bearing mice, Sarcoma 180 cells were transplanted in the muscle of the hind leg of the mice ($1 \times 10^7$ cells/mouse) 7 days before the start of administration of the RDP substance and, thereafter, the mice were tested in the same manner as above. The results are shown in the Table II.

TABLE II

| Sample | Dose (mg/kg) | Normal Mice | | Tumor-bearing Mice | |
|---|---|---|---|---|---|
| | | Phagocytic Index | Relative Value (%) | Phagocytic Index | Relative Value (%) |
| Control (Saline) | — | $42.8 \times 10^{-3}$ | 100 | $101 \times 10^{-3}$ | 100 |
| RDP Substance | 10 | 53.7 | 125 | 110 | 109 |
| | 30 | 94.2 | 220 | 150 | 149 |
| | 100 | 86.5 | 202 | 130 | 129 |

It can be seen from the results shown in the Table II that for both of the normal and the tumor-bearing mice the administration of the RDP substance in an amount of from 10 to 100 mg/kg, particularly in 30 mg/kg enhanced the function of the reticuloendothelial system of the mice and greatly intensified the phagocytic activity of macrophage.

(b) Plaque-forming Cell Test (PFC)

This method is used to examine the effect of the RDP substance to enhance the antibody-producing ability due to the activation of B cells of the host amongst the immunomodulating actions.

The RDP substance dissolved in a saline was administered intraperitoneally to a test group of six 4-week-old female ICR-CRJ mice (average weight, 20 g) for 3 consecutive days. For the control group, only a saline was administered in the same manner. At the fourth day and also the eleventh day, sheep red blood cells were injected into the tail vein ($4 \times 10^8$ cells/mouse) to sensitize the mice. Four days after the injection, the plaque-forming ability of the spleen cells of mice was determined by the method of Cunningham. The results are shown in the Table III.

It can be seen from the results shown in the Table III that the administration of the RDP substance in a dose of 10 to 100 mg/kg greatly enhanced the antibody-producing ability in mice.

(c) Delayed Type Hypersensitivity Reaction (DHR)

This method is used to examine the effect of the RDP substance to enhance the action of cell-mediated immunity due to the activation of T cells of the host amongst the immunomodulating actions.

The RDP substance dissolved in a saline was administered orally to a test group of six 8-week-old ICR-CRJ mice (female; average weight: 27 g) for 8 consecutive days. For the control group, on the other hand, only a saline was administered in the same manner. At the fourth day from the administration, a 5% ethanol solution of picryl chloride was coated on the abdominal region which had been shaved to achieve a primary sensitization. At the eleventh day, a 1% olive oil solution of picryl was coated on the obverse and reverse side of the each ear of the mouse to accomplish a secondary sensitization. After 24 hours, an increase in the thickness of the ears was measured by means of a gauge; that is, the increase in the thickness of the ear was determined by measuring the difference in thickness between before coating and after coating. On the other hand, in the case of tumor-bearing mice, Sarcoma 180 were transplanted intraperitoneally ($1 \times 10^5$ cells/mouse) prior to the administration of the RDP substance and, thereafter, the same procedure as above was repeated.

The results are shown in the Table IV.

TABLE IV

| Sample | Dose (mg/kg) | Normal Mice | | Tumor-bearing Mice | |
|---|---|---|---|---|---|
| | | Increase in Ear Thickness (mm) | Relative Value (%) | Increase in Ear Thickness (mm) | Relative Value (%) |
| Control (Saline) | — | $3.39 \times 10^{-2}$ | 100 | $0.94 \times 10^{-2}$ | 100 |
| RDP Substance | 30 | 8.30 | 245 | 2.40 | 255 |
| | 100 | 8.14 | 240 | 2.35 | 250 |
| | 500 | 5.86 | 173 | 2.08 | 221 |

It can be seen from the results shown in the Table IV that the RDP substance administered orally in a dose of 30 to 500 mg/kg enhanced greatly the cell-mediated immunity in the both case of normal and tumor-bearing mice.

From the results of the above-described tests (a), (b) and (c), it can be seen that the RDP substance enhances greatly various immunity actions in mice having different mechanisms. The immunomodulating agent can be used in cases in which the immunity function falls down or the recognizing function against the foreign antigen is poor. Thus the RDP substance is expected to find uses as, for example, a therapeutic agent or an adjuvant therapeutic agent or a preventing agent or an agent for acceleration of recuperation after operation for infectious diseases and malignant tumors.

In addition to the above-described immunity activating or recovering capability, the imnunomodulating agent may be used sometimes to normalize the abnormally stimulated immunity reaction; for example, may be applied to self immunity diseases such as rheumatism, collagen diseases, and allergy.

(3) Host Defense Activity

It is well known that the host defense activities of living body against the bacterial infectious diseases are based on the following principles: one is so-called the humoral immunity depending on the production of antibody against the invaded bacteria and another is so-called the cell-mediated immunity in which macrophage and T cell fight against the invaded bacteria. In general, the living body has a sufficient host defense activities against the invasion of such foreign bacteria. However, it is well known that in the tumor-bearing condition, particularly in the later stage of cancer, those activities fall down seriously, therefore, that the serious damage is caused even by some non-pathogenic bacteria usually living together in the host.

In order to determine if the RDP substance enhances the mice host defense activities of the host against infectious diseases due to such bacteria, the inhibitory activity of the RDP substance against the infection of *Escherichia coli*, a typical infectious microorganism against which is said the humoral immunity might participiate, and against the infection of *Listeria monocytogenes*, which is said the cell-mediated immunity might participate, are examined.

Seven-week-old ICR-CRJ mice (female; average weight: 26 g) were divided into four groups of 20 mice each. The RDP substance dissolved in a saline was injected subcutaneously in the back of the mice in a dose of 10, 30 or 100 mg/kg, at 3 days and one day before the infection. For the control group, only a saline was injected in the same manner. Then, in the case of *E. coli*, $2 \times 10^7$ cells/mouse were infected subcutaneously in the back, and in the case of *L. monocytogenes*, $2 \times 10^7$ cells/mouse were infected intraperitoneally. After one week, the number of survival was compared. The protective effect was calculated by the following equation:

$$\text{Protective Effect (\%)} = \frac{\text{Number of survival in test group} - \text{Number of survival in control group}}{\text{Number of mice in one group}} \times 100$$

The results are shown in the Table V.

TABLE V

| | | | Administration Time Before Infection | | | |
|---|---|---|---|---|---|---|
| | | | One Day Before | | 3 Days Before | |
| Bacteria | Sample | Dose (mg/kg) | No. of Survival | Protective Effect (%) | No. of Survival | Protective Effect (%) |
| *E. coli* SB-001 | Control (Saline) | — | 0 | — | 0 | — |
| | RDP Substance | 10 | 16 | 80 | 17 | 85 |
| | | 30 | 18 | 90 | 19 | 95 |
| | | 100 | 20 | 100 | 20 | 100 |
| *L. mono.* SB-010 | Control (Saline) | — | 0 | — | 0 | — |
| | RDP Substance | 10 | 8 | 40 | 8 | 40 |
| | | 30 | 12 | 60 | 12 | 60 |
| | | 100 | 10 | 50 | 10 | 50 |

It can be seen from the results shown in the Table V that the administration of the RDP substance in a dose of 10 to 100 mg/kg prior to infection generates very strong host defense activities against the infection of *E. coli* and also significant activities against that of *L. monocytogenes*.

In view of the fact that the RDP substance is of no toxicity, this substance is expected to be a very useful host defense agent against infectious disease.

The acute toxicity of the RDP substance will hereinafter be described in detail.

Ten 5-week-old SD-CRJ rats (male; weight: 120–150 g) were used in the control and test group respectively. The RDP substance was administered once at the physically maximum dose of 15 g/kg in the test group, and only a saline in the control group. No rat died. The increase of weight in the test group was equal to that in the control group. Furthermore, no abnormality was observed in both appearance and necropsy. Thus it is considered that the $LD_{50}$ of this substance is larger than 15 g/kg and the substance has no acute toxicity.

In accordance with the present invention, the polysaccharide RDP substance exhibiting superior antitumor and immunomodulating activities in mice, and host defense activity in mice against infections microorganisms as described above can be obtained in a large amount, as demonstrated in Examples described hereinafter, by a combination of relatively easy procedures. Thus the present invention has a high practical value in the field of a commercial production of a polysaccharide from rice bran with excellent biological activities.

Furthermore, since the RDP substance of the present invention is observed to have, an, interferon-inducing ability, it is expected to have activity in preventing or treating against virus diseases such as herpes and influenza.

Since the RDP substance can be administered both orally and non-orally, it is expected to be a very useful antitumor against transplantable tumors, immunomodulating, or infectious disease-preventing or treating agent.

In the practical form of the drug, the RDP substance can be produced singly or in combination with adjuvants (e.g., water, saline, polyethylene glycol, glycerogelatin, starch, dextrin, lactose, etc.) in the form of, e.g., liquid medicine, pellet, tablet, powder, and suppository etc.

The present invention is described in detail with reference to the following examples.

EXAMPLE 1

Tap water (125 liters) was added to 25 kg of commercially available rice bran which had been separated from rice pieces and so forth by passing through a screen. The mixture was extracted at 120° C. for 1 hour and 100° C. for 5 hours with constant stirring.

The mixture was then filtered. The filtrate was concentrated under a reduced pressure to 40 liters. The thusconcentrated filtrate was adjusted to pH 6.7 with sodium hydroxide and, thereafter, 500 mg of an $\alpha$-amylase (produced by Nagase Sangyo Co., Ltd.) was added and an enzyme treatment was performed at 70° C. for 1 hour. After the enzyme treatment, the enzyme was inactivated by heating up to 100° C., and insolubles were removed by centrifugation. Ethanol was added to the final concentration of 30% (v/v). The precipitate formed was separated. This precipitate was dissolved again in water to remove insolubles. The soluble part was lyophilized and 508g of a light yellow powder was obtained. Four grams of the said powder was dissolved again in ionexchanged water, and insolubles were removed by centrifugation. The soluble part was applied on a gel filtration of Sepharose CL-6B (produced by Pharmacia Chemicals AB), and fractions eluted in the void volume were collected and lyophilized to obtain 1 g of a white powder. This white powder was dissolved again in 100 ml of ion-exchanged water and placed in a separatory funnel along with 20 ml of chloroform and 4 ml of n-butanol. The mixture was shaken for 60 minutes and then centrifuged at a low speed, whereupon a white layer of denatured protein was formed between a water layer and a chloroform layer. The water layer portion was taken out of the separatory funnel. A chloroform/n-butanol mixture of the same ratio as above was added, and the resulting mixture was shaken. This operation was repeated about 30 times until the white layer of the denatured protein did not occur. The water layer portion was lyophilized to obtain 800 mg of a white deproteinized powder.

EXAMPLE 2

Commercially available rice bran (25 kg) was defatted by refluxing with 100 liters of hexane and then dried. The defatted rice bran was then treated in the same manner as in Example 1 to obtain 450 g of a light yellow powder. Four grams of the said powder was treated in the same manner as in Example 1 to obtain 750 mg of a white powder.

EXAMPLE 3

Commercially available defatted rice bran (3 kg) was mixed with 20 liters of water, and the mixture was then extracted at 120° C. for 2 hours with constant stirring. The mixture was concentrated under a reduced pressure to obtain 5 liters of a concentrated solution. Then, 0.3 g of an $\alpha$-amylase was added to the solution, and it was maintained at 60° C. for 5 hours. Thereafter, the mixture was heated to 100° C. and was subjected to centrifugation to get 4.9 liters of a supernatant. Ethanol was added to the final concentration of 40% (v/v). The precipitate formed was separated and then lyophilized to obtain 88 g of a light yellow-brown powder.

Four grams of the said powder was treated in the same manner as in Example 1 to obtain 720 mg of a white powder.

EXAMPLE 4

Commercially available rice bran (20 kg) was passed through a 30-mesh screen to remove contaminants such as rice pieces, and then washed with 100 liters of ion-exchanged water. Then, 50 liters of distilled water was added to the above-washed rice bran, and the mixture was extracted at 110° C. for 3 hours with constant stirring. The mixture was filtered. The filtrate was concentrated under a reduced pressure and centrifuged, whereupon 10 liters of a supernatant was obtained. Then, 250 mg of an $\alpha$-amylase was added to it and kept at 65° C. for 24 hours. The mixture was heated to 100° C. Ethanol was then added to the final concentration of 30% (v/v). The precipitate formed was separated. This precipitate was dissolved again in 3 liters of water, and insolubles were removed, and concentrated again to 1 liter, and centrifuged to get a supernatant. This supernatant was dialyzed for 2 days with running water and centrifuged to get 1 liter of a supernatant. A mixture of 200 ml of chloroform and 40 ml of n-butanol was added to 1 liter of the said supernatant. Thereafter, a deproteinization and a lyophilization were performed in the same manner as in Example 1 to obtain 402 g of a white powder.

EXAMPLE 5

A supernatant (1 liter) as obtained by dialysis and centrifugation in Example 1 was applied on ion exchange chromatography using CM Sepharose, a cation exchange gel, and DEAE Sepharose, an anion exchange gel. Fractions not adsorbed were collected and concentrated to 1 liter. Thereafter, a deproteinization and a lyophilization were performed in the same manner as in Example 1 to obtain 358 g of a white powder.

EXAMPLE 6

Activated carbon (10 g) was added to 1 liter of a supernatant as obtained by dialysis and centrifugation in Example 1. After 30 minutes, the mixture was centrifuged. The supernatant was subjected to the same deproteinizing and lyophilizing treatment as in Example 4 to obtain 365 g of a white powder.

EXAMPLE 7

A 20 ml portion of 1 liter of a supernatant as obtained by dialysis and centrifugation in Example 4 was applied on gel filtration using Sepharose CL-6B, and void volume fractions were collected to make up 100 ml. This liquid was subjected to the same deproteinizing and lyophilizing treatment as in Example 1 to obtain 70 g of a white powder.

EXAMPLE 8

The precipitate obtained by the ethanol precipitation after an $\alpha$-amylase treatment in Example 1 was dissolved again in 10 liters of water. The solution was applied on an ultrafiltration to remove the low molecular part lower than 80,000 (molecular weight), and also to concentrate to 3 liters. The precipitate formed was removed by centrifugation, yielding 2.8 liters of a supernatant. This supernatant was subjected to the same deproteinizing and lyophilizing treatment as in Example 1 to obtain 400 g of a white powder.

EXAMPLE 9

To the solution subjected to the α-amylase treatment followed by the inactivation of the enzyme at 100° C. for 1 hour in Example 1 acetone was added to the final concentration of 40% (v/v). The precipitate formed was dissolved in 10 liters of water. Thereafter, the same procedure including the treatment using an ultrafilter as in Example 8 was applied to obtain 412 g of a white powder.

EXAMPLE 10

To the solution subjected to the α-amylase treatment followed by the inactivation of the enzyme at 100° C. for 1 hour in Example 1 ammonium sulfate was added to the degree of saturation of 70% to achieve salting-out. The precipitate formed was collected by centrifugation, dissolved in 3 liters of water, and dialyzed against running water for 2 days. Trichloroacetic acid was added to the said solution to the concentration of 7%. The precipitate formed was removed by centrifugation. The supernatant was dialyzed again against the running water for 2 days. The thus-obtained dialyzate was lyophilized to obtain 503 g of a light yellow powder. Four grams of the powder was dissolved in ion-exchanged water and passed through a column of Sepharose CL-6B. Void volume fractions were collected and lyophilized to obtain 1.5 g of a white powder.

EXAMPLE 11

The solution subjected to the α-amylase treatment in Example 1 was cooled to 40° C., and 600 mg of a proteinase (Pronase E, produced by Kaken Kagaku Co., Ltd.) was then added and was allowed to react for 24 hours. The reaction mixture was heated at 100° C. for 1 hour to inactivate the enzyme. Insolubles were removed by centrifugation. To the supernatant ethanol was added to the final concentration of 30% (v/v). The precipitate formed was collected by centrifugation and then dissolved in 10 liters of water. Thereafter, the same procedure including the treatment using an ultrafilter as in Example 8 was applied to obtain 413 g of a white powder.

EXAMPLE 12

To 3 liters of the supernatant obtained by the treatment using an ultrafilter in Example 8, a mixture of chloroform and n-butanol of the same ratio as in Example 1 was added to perform a deproteinizing treatment. A water-soluble portion was spray-dried to obtain 420 g of a white powder.

EXAMPLE 13

To the water-soluble portion obtained by applying the deproteinizing treatment in Example 12, ethanol was added to the final concentration of 40% (v/v). The precipitate formed was collected by centrifugation, washed and dehydrated three times with ethanol, and then dried in vacuo to obtain 405 g of a white powder.

EXAMPLE 14

To 2 g of a white powder obtained in the Example 5, 100 ml of 2% sulfuric and formic acid mixture was added, and kept for 4 hours at 60° C. to hydrolyze it. The solution was neutralized by adding barium carbonate, and centrifuged, and a supernatant was obtained.

A half volume of the supernatant was applied on Sepharose CL-2B, and the fraction $F_1$ (molecular weight: >20,000,000) eluting in the void volume and the fraction $F_2$ (molecular weight: about 1,000,000) were collected. Another half volume of the supernatant was applied on Sephadex G-200 (produced by Pharmacia Chemicals AB), and the fraction $F_3$ (molecular weight: about 100,000) and the fraction $F_4$ (molecular weight: about 10,000) were collected. White powders, $F_1$: 412 mg, $F_2$: 248 mg, $F_3$: 295 mg, and $F_4$: 263 mg were obtained by lyophilizing each solution.

Biological activities of each fraction were tested using the method described above. All the 4 fractions showed the activities as strong as the RDP substance before hydrolyzation. The results are shown in detail as follows:

(1) Antitumor Activities

The activities against a syngeneic tumor, Meth-A, by oral administration are shown in Table VI.

TABLE VI

| Fraction | Dose (mg/kg) | Average Tumor weight (g) | Inhibition Ratio (%) |
|---|---|---|---|
| Control (Saline) | — | 8.60 | — |
| $F_1$ | 30 | 4.90 | 43 |
| $F_2$ | " | 5.16 | 40 |
| $F_3$ | " | 5.33 | 38 |
| $F_4$ | " | 5.30 | 38 |

(2) Immunomodulating Activities (a) Carbon Clearance Test (CCT)

The activities using tumor-bearing mice are shown in Table VII.

TABLE VII

| Fraction | Dose (mg/kg) | Phagocytic Index | Relative Value (%) |
|---|---|---|---|
| Control (Saline) | — | $111 \times 10^{-3}$ | 100 |
| $F_1$ | 30 | 153 | 138 |
| $F_2$ | " | 155 | 140 |
| $F_3$ | " | 158 | 142 |
| $F_4$ | " | 150 | 135 |

(b) Plaque Forming Cell Test (PFC)

The activities using normal mice sensitized at 4th day by sheep red blood cells are shown in Table VIII.

TABLE VIII

| Fraction | Dose (mg/kg) | Plaque Number Spleen | Relative Value (%) |
|---|---|---|---|
| Control (Saline) | — | $2.6 \times 10^4$ | 100 |
| $F_1$ | 30 | 6.0 | 231 |
| $F_2$ | " | 5.5 | 212 |
| $F_3$ | " | 5.2 | 200 |
| $F_4$ | " | 5.0 | 192 |

(c) Delayed Type Hypersensitivity Reaction (DHR)

The activities using tumor-bearing mice are shown in Table IX.

TABLE IX

| Fraction | Dose (mg/kg) | Increase in Ear Thickness (mm) | Relative Value (%) |
|---|---|---|---|
| Control (Saline) | — | $0.90 \times 10^{-2}$ | 100 |
| $F_1$ | 30 | 2.07 | 230 |
| $F_2$ | " | 2.21 | 245 |
| $F_3$ | " | 1.89 | 210 |
| $F_4$ | " | 1.80 | 200 |

(3) Host Defense Activities Against Infectious Deseases

The activities administered subcutaneously one day before infection are shown in Table X.

TABLE X

| | | E. coli*1 | | L. mono.*2 | |
|---|---|---|---|---|---|
| Fraction | Dose (mg/kg) | Number of Survival | Protective Effect (%) | Number of Survival | Protective Effect (%) |
| Control (Saline) | — | 0 | — | 0 | — |
| $F_1$ | 30 | 20 | 100 | 12 | 60 |
| $F_2$ | " | 18 | 90 | 10 | 50 |
| $F_3$ | " | 17 | 85 | 10 | 50 |
| $F_4$ | " | 17 | 85 | 9 | 45 |

E. coli*1: Escherichia coli SB-001
L. mono.*2: Listeria monocytogenes SB-010

What is claimed is:

1. A polysaccharide RDP substance, (1) having the following properties:

it does not pass through a dialysis membrane;
it is insoluble in alcohol, acetone, hexane, benzene, ethyl acetate, dimethylsulfoxide, ligroin, carbon tetrachloride, chloroform, and ether, and is soluble in water;
a 1% aqueous solution is neutral;
it contains minerals in an amount not more than 5%;
it reacts positively in the following reactions: the Molisch reaction, anthrone-sulfuric acid reaction, tryptophansulfuric acid reaction, cystein-sulfuric acid reaction, chromotropesulfuric acid reaction, phenol-sulfuric acid reaction, and carbazole-sulfuric acid reaction; and negatively in biuret reaction, ninhydrin reaction, the Lowry-Folin reaction, the Elson-Morgan reaction, and starch-iodine reaction;
it has an ultraviolet absorption spectrum as shown in FIG. 1, an infrared absorption spectrum as shown in FIG. 2, and a $13_{C-NMR}$ spectrum as shown in FIG. 3; and (2) said polysaccharide RDP substance is substantially protein free consists essentially of glucose as the sole sugar component with $\alpha$-1,6-glucoside bonds as the main chain and it also contains a much smaller amount of $\alpha$-1,4-glucoside bonds.

2. A pharmaceutical composition effective in inhibiting the growth of transplantable tumors, having immunomodulating activity and in potentiating the host defense ability of mice against infectious microorganisms comprising an effective amount of a polysaccharide RDP substance and a pharmaceutically acceptable vehicle, said polysaccharide RDP substance (1) having the following properties:

it does not pass a dialysis membrane;
it is insoluble in alcohol, acetone, hexane, benzene, ethyl acetate, dimethylsulfoxide, ligroin, carbon tetrachloride, chloroform, and ether, and is soluble in water;
a 1% aqueous solution is neutral;
it contains minerals in an amount not more than 5%;
it reacts positively in the following reactions: the Molisch reaction, antrhone-sulfuric acid reaction, tryptophansulfuric acid reaction, cystein-sulfuric acid reaction, chromotropesulfuric acid reaction, phenol-sulfuric acid reaction, and carbazole-sulfuric acid reaction; and negatively in biuret reaction, ninhydrin reaction, the Lowry-Folin reaction, the Elson-Morgan reaction, and starch-iodine reaction;
it has an ultraviolet absorption spectrum as shown in FIG. 1, an infrared absorption spectrum as shown in FIG. 2, and a $13_{C-NMR}$ spectrum as shown in FIG. 3; and (2) said polysaccharide RDP substance is substantially protein free and consists essentially of glucose as the sole sugar component with $\alpha$-1,6-glucoside bonds as the main chain and it also contains a much smaller amount of $\alpha$-1,4-glucoside bonds.

* * * * *

UNITED STATES PATENT AND TRADEMARK OFFICE
CERTIFICATE OF CORRECTION

PATENT NO. : 4,764,507
DATED : August 16, 1988
INVENTOR(S) : TAKEO et al

It is certified that error appears in the above-identified patent and that said Letters Patent is hereby corrected as shown below:

In the title page, the name of the first Assignee should read as follows:

--Sapporo Breweries Limited--.

Signed and Sealed this

Eighteenth Day of December, 1990

Attest:

HARRY F. MANBECK, JR.

Attesting Officer

Commissioner of Patents and Trademarks